United States Patent
Tayebi et al.

(10) Patent No.: US 11,026,794 B2
(45) Date of Patent: Jun. 8, 2021

(54) REINFORCED BONE SCAFFOLD

(71) Applicant: Marquette University, Milwaukee, WI (US)

(72) Inventors: Lobat Tayebi, Milwaukee, WI (US); Morteza Rasoulianboroujeni, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 0 days.

(21) Appl. No.: 16/092,672

(22) PCT Filed: May 2, 2017

(86) PCT No.: PCT/US2017/030555
§ 371 (c)(1),
(2) Date: Oct. 10, 2018

(87) PCT Pub. No.: WO2017/192525
PCT Pub. Date: Nov. 9, 2017

(65) Prior Publication Data
US 2019/0167431 A1 Jun. 6, 2019

Related U.S. Application Data (60) Provisional application No. 62/330,561, filed on May 2, 2016.

(51) Int. Cl.
| | | |
|---|---|---|
| A61F 2/28 | (2006.01) |
| A61L 27/58 | (2006.01) |
| A61L 27/18 | (2006.01) |
| A61L 27/20 | (2006.01) |
| A61L 27/22 | (2006.01) |
| A61L 27/24 | (2006.01) |
| A61L 27/42 | (2006.01) |
| A61L 27/46 | (2006.01) |
| A61L 27/48 | (2006.01) |
| A61L 27/54 | (2006.01) |
| A61L 27/56 | (2006.01) |
| A61K 38/18 | (2006.01) |
| A61F 2/30 | (2006.01) |

(52) U.S. Cl.
CPC ............ *A61F 2/28* (2013.01); *A61K 38/1875* (2013.01); *A61L 27/18* (2013.01); *A61L 27/20* (2013.01); *A61L 27/222* (2013.01); *A61L 27/225* (2013.01); *A61L 27/24* (2013.01); *A61L 27/425* (2013.01); *A61L 27/46* (2013.01); *A61L 27/48* (2013.01); *A61L 27/54* (2013.01); *A61L 27/56* (2013.01); *A61L 27/58* (2013.01); *A61F 2/30942* (2013.01); *A61F 2002/30011* (2013.01); *A61F 2002/30032* (2013.01); *A61F 2002/30075* (2013.01); *A61F 2002/3092* (2013.01); *A61F 2002/30962* (2013.01); *A61F 2310/00365* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 6,283,997 B1 | 9/2001 | Garg et al. | |
| 6,454,811 B1 * | 9/2002 | Sherwood | A61F 2/28 623/23.76 |
| 8,999,377 B2 * | 4/2015 | Rolfes | A61L 15/28 424/426 |
| 9,504,574 B2 * | 11/2016 | Farrar | A61L 24/0036 |
| 2003/0072790 A1 | 4/2003 | Tsai et al. | |
| 2005/0042253 A1 | 2/2005 | Farrar et al. | |
| 2006/0105011 A1 | 5/2006 | Sun et al. | |
| 2008/0097606 A1 | 4/2008 | Cragg et al. | |
| 2010/0255447 A1 * | 10/2010 | Biris | A61C 8/0013 433/201.1 |

FOREIGN PATENT DOCUMENTS

| | | |
|---|---|---|
| EP | 0727232 A2 | 8/1996 |
| JP | 2007503226 A | 2/2007 |
| JP | 2009513280 A | 4/2009 |
| JP | 2009095522 A | 5/2009 |
| JP | 2012016517 A | 1/2012 |
| JP | 2015089433 A | 5/2015 |
| WO | 2009120886 A2 | 10/2009 |
| WO | WO-2009120886 A2 * | 10/2009 ......... A61B 17/8645 |

OTHER PUBLICATIONS

International Search Report and Written Opinion in corresponding PCT Application No. PCT/US2017/030555 dated Aug. 24, 2017.
Extended European Search Report for European Patent Application No. 17793114.4, dated May 26, 2020.
Notice of Reasons for Refusal for Japanese Patent Application No. 2018-554440, drafted Mar. 10, 2021.

* cited by examiner

*Primary Examiner* — Celeste A Roney
(74) *Attorney, Agent, or Firm* — Andrus Intellectual Property Law, LLP (57) ABSTRACT

Scaffolds for use in bone tissue engineering include a skeleton and a host component. Methods of preparation of scaffolds include identification of biodegradation properties for the skeleton and the host component. The skeleton is constructed to form a three-dimensional shape. The skeleton is constructed of a first material and has a first rate of biodegradation. The host component fills the three-dimensional shape formed by the skeleton. The host component is constructed of a second material and has a second rate of biodegradation. The first rate of biodegradation is slower than the second rate of biodegradation.

11 Claims, 10 Drawing Sheets

REINFORCED BONE SCAFFOLD

CROSS REFERENCE TO RELATED APPLICATION

This application is the U.S. national stage application of International Application PCT/US2017/030555, filed May 2, 2017, which international application was published on Nov. 9, 2017, as International Publication WO2017/192525 in the English language. The international application is incorporated herein by reference, in entirety. The international application claims priority to U.S. Provisional Patent Application No. 62/330,561, filed on May 2, 2016, the contents of which is hereby incorporated herein by reference in its entirety.

BACKGROUND

The present disclosure is related to the field of bone tissue engineering. More specifically, the present disclosure is related to a scaffold for in vivo bone tissue engineering.

Commonly people will suffer at least one bone fracture during their lifetime. Still, other people will suffer from bone defects or loss due to injury, disease, or genetic defect. Tissue engineering solutions in the field of bone tissue growth have advanced over the last two decades. Typically, a porous material is used as a scaffold upon which new bone cells grow. In some solution, the porous scaffold is further constructed of a biodegradable material such that the scaffold degrades and/or dissolves in the body over time.

However, the inventors have discovered that there are limitations to currently available bone growth scaffolds. First, currently porous and biodegradable scaffolds are weak in mechanical strength. Both porosity and biodegradability are qualities that are contrary to mechanical strength of the scaffold. When the size of the bone damage or defect is small, the scaffold and new bone tissue can rely upon the strength of the existing bone tissue surrounding the damage or defect. However, as the size of the damage of defect increases or the location of the damage or defect is particularly load bearing, external sources of mechanical strength are required until the new bone has regrown. Other currently available solutions may use metal plates, pins, or screws in and around the area of damage or defect. However, these solutions either permanently reside in the body of the patient, or must be later removed, requiring additional surgery and/or damage to the surrounding tissue. Furthermore, such metal or composite structures may induce allergic reaction in some patients.

BRIEF DISCLOSURE

An exemplary embodiment of a scaffold for use in bone tissue engineering includes a skeleton and a host component. The skeleton is constructed to form a three-dimensional shape. The skeleton is constructed of a first material and has a first rate of biodegradation. The host component fills the three-dimensional shape formed by the skeleton. The host component is constructed of a second material and has a second rate of biodegradation. The first rate of biodegradation is slower than the second rate of biodegradation.

In a further exemplary embodiment of the scaffold, the skeleton and the host component are a unitary structure with the host component having a greater porosity than the skeleton. In another exemplary embodiment, the host component further includes bone morphogenetic proteins. In a still further exemplary embodiment, the skeleton has a first porosity and the host component has a second porosity and the second porosity being greater than the first porosity. In another embodiment, the first porosity may be the same or greater than the second porosity, for example in embodiments wherein the rates of biodegradation are dependent upon other physical properties, including but not limited to material selection.

An exemplary embodiment of a method of preparing a scaffold for use in bone tissue engineering includes obtaining a 3D model of a treatment area of a patient. A desired degradability of the scaffold is determined based upon the patient and the treatment area. At least one skeleton characteristic is selected and at least one host component characteristic is selected to achieve the desired degradability. The skeleton is digitally designed to fit the treatment area. The skeleton is manufactured with the at least one skeleton characteristic. The skeleton is filled with a host component having the at least one host component characteristic.

In a further exemplary embodiment of the method of preparing a scaffold, the at least one skeleton characteristic includes at least one of a base material, a material processing technique, a porosity, and a pore size. In the exemplary embodiment, at least one host component characteristic includes at least one of a base material, a material processing technique, a porosity, and a pore size. In another exemplary embodiment, manufacturing the skeleton includes 3D printing the skeleton.

In an exemplary embodiment, the host component is a foam and the method further includes freeze-drying the skeleton filled with the host component to create the scaffold. In further exemplary embodiment, at least one material of the host component is selected. A solution of the at least one material of the host component is created. The solution is agitated to produce a host component foam. The host component foam is molded into the skeleton. The skeleton filled with the host component foam is frozen. The frozen skeleton and the host component foam are freeze-dried to produce the scaffold.

DETAILED DISCLOSURE

Tissue engineering is well-known as a recent approach for repair, replacement or regeneration of tissues and organs that are damaged through traumatic injuries, aging or illness. In the last two decades, tissue engineering methods have had very successful outcomes in regenerating skin, cartilage, and bone tissues. The number of bone fractures in the U.S. exceeds 6.2 million each year. Unfortunately, in 10% of these cases the healing procedure is not successful due to non-union or delayed union. Interventional remedies to treat these unsuccessful procedures amounts to significant additional healthcare expenses, and lost patient time for subsequent recovery.

Different methods have been utilized to meet this huge demand for bone healing. Autografts are the gold-standard treatment for repairing bone injuries. The major problem with this approach is the limited supply and donor site morbidity. Alternatively, bone allografts can be used instead of autografts. However, there are serious cost issues and the risk of disease transmission in using bone allografts. Metallic implants are also widely used in bone treatment especially for large bone defects. But unlike natural bone, they are not self-repairing material. Also, they do not adjust with alterations in physiological conditions. More importantly the implants can become movable and loose over time.

The deficiencies of the above approaches have made bone tissue engineering very popular in the last decade. The most important obligation of tissue engineers is developing scaffolds. A good scaffold is biocompatible and biodegradable. Its structure is highly porous with good stiffness and strength. The goal in designing scaffolds for bone tissue engineering is to mimic the morphology, structure and function of bone. Currently, different kinds of bio materials have been utilized for this purpose, embodies of which may be synthetic or naturally derived. Tissue engineering scaffolds should consist of interconnected macro-porous networks allowing cell migration, nutrient delivery, and eventually vascularization. However, the porosity significantly decreases the mechanical strength of the scaffolds, which is crucial, especially for large bone defects.

Note that spontaneous renewal of the bone is limited to fairly small defects. Large bone defects caused by tumors, trauma, implant loosening, or osteitis requires surgical therapy. The reconstruction of large bone segments is an important clinical challenge. Despite this, improved solutions in the field are still needed.

Figure 1:
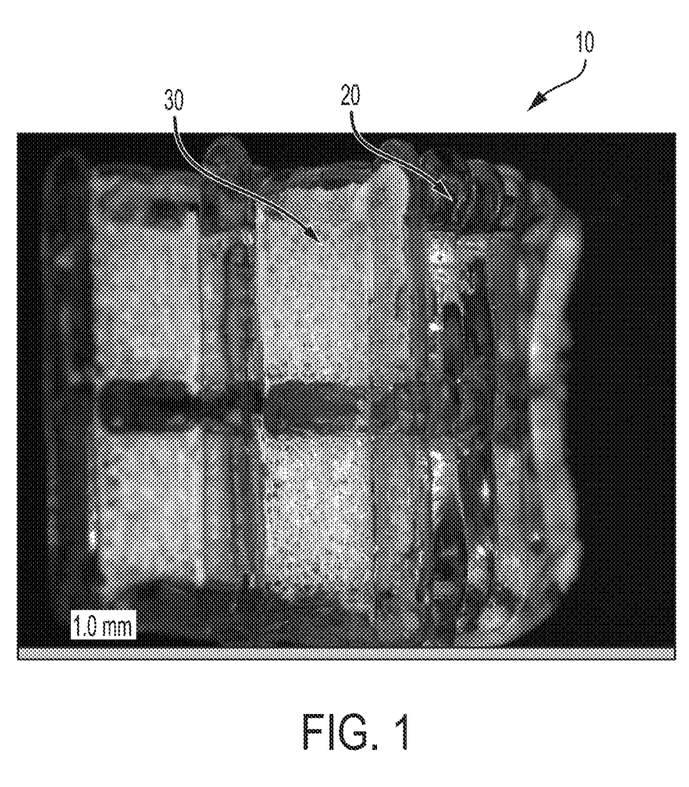
FIG. 1 depicts an exemplary embodiment of a scaffold.

FIG. 1 depicts an exemplary embodiment of a scaffold 10 as disclosed herein. The scaffold 10 is generally constructed of two components, a skeleton 20 and a host component 30. The skeleton 20 is exemplarily depicted on its own in FIG. 2 without the host component 30 to better show the skeleton 20. The skeleton 20 is exemplarily constructed of a material with a high mechanical strength, biocompatible, and while biodegradable, is biodegradable over a comparatively longer time than the host component 30. It will be recognized that in exemplary embodiments porosity, thickness, and material composition can all contribute to the degradability of the skeleton 20 and/or the host component 30 of the scaffold 10. In embodiments, a material or materials are selected for the skeleton 10 which are biocompatible, provide strong mechanical properties, and provide a comparatively slower biodegradability when compared to the biodegradability of the host component 30. This skeleton 20 is combined with a host component 30 that is selected for its bioactivity properties and promotion of growth of new bone tissue. The host component 30 of the scaffold 10 functions to promote tissue growth and diffusion of nutrients and waste. In an embodiment, the host component 30 includes bone morphogenetic proteins (BMP) which may be used in embodiments to accelerate bone tissue growth. Previous bone tissue scaffolds have focused on the use of materials, rather than the structure of the scaffold itself. Table 1 presents a variety of proposed materials, for bone tissue scaffolds along with the resultant mechanical properties and porosity thereof.

FIGS. 3A-3E all depict various exemplary embodiments of scaffold skeletons 20 as may be used in exemplary embodiments of the scaffold as disclosed herein.

Figure 2:
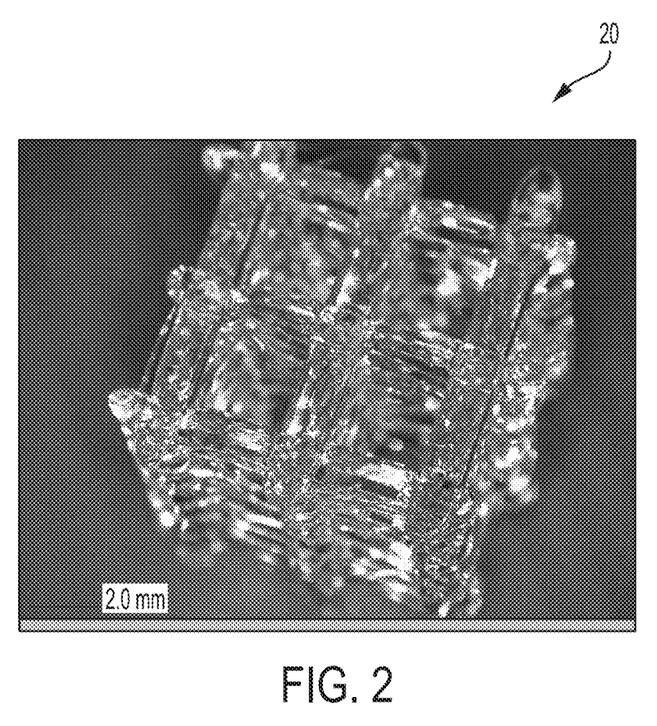
FIG. 2 depicts an exemplary embodiment of a skeleton without the host component.
Figure 3A:
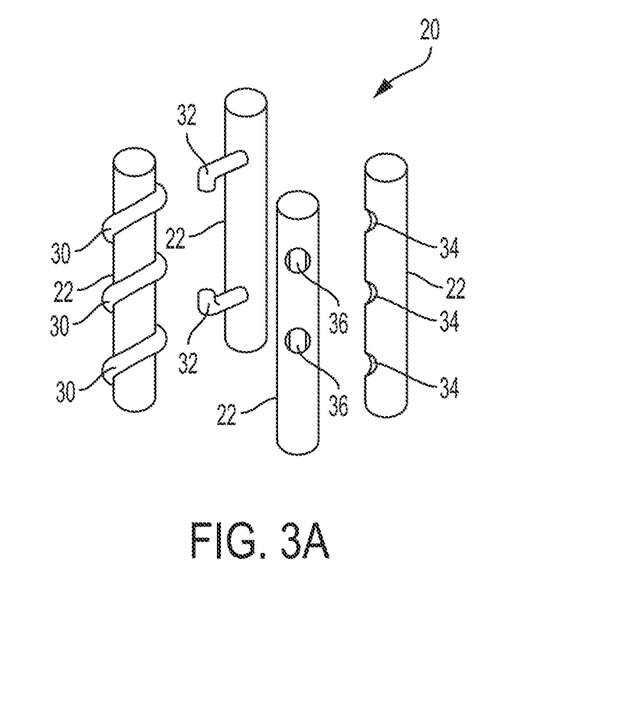
FIGS. 3A-F depict various exemplary embodiments of skeleton configurations.
Figure 3B:
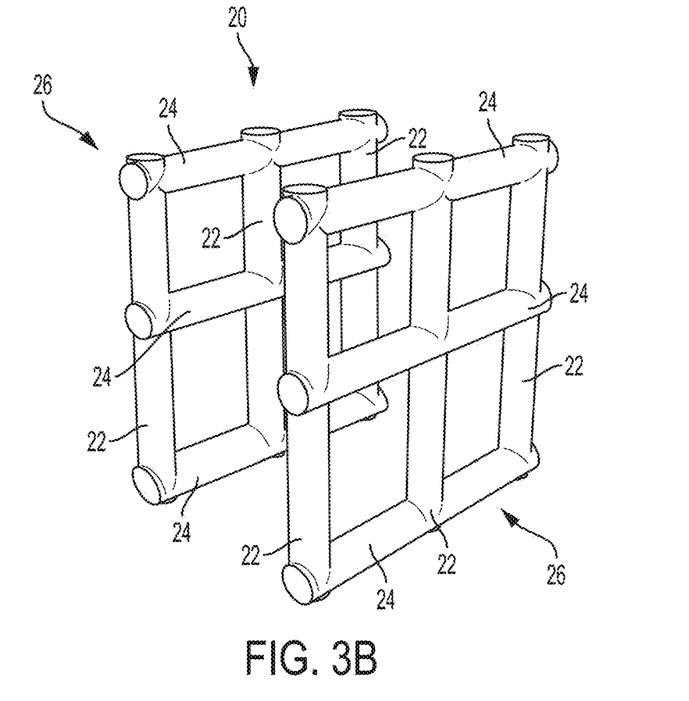
Figure 3C:
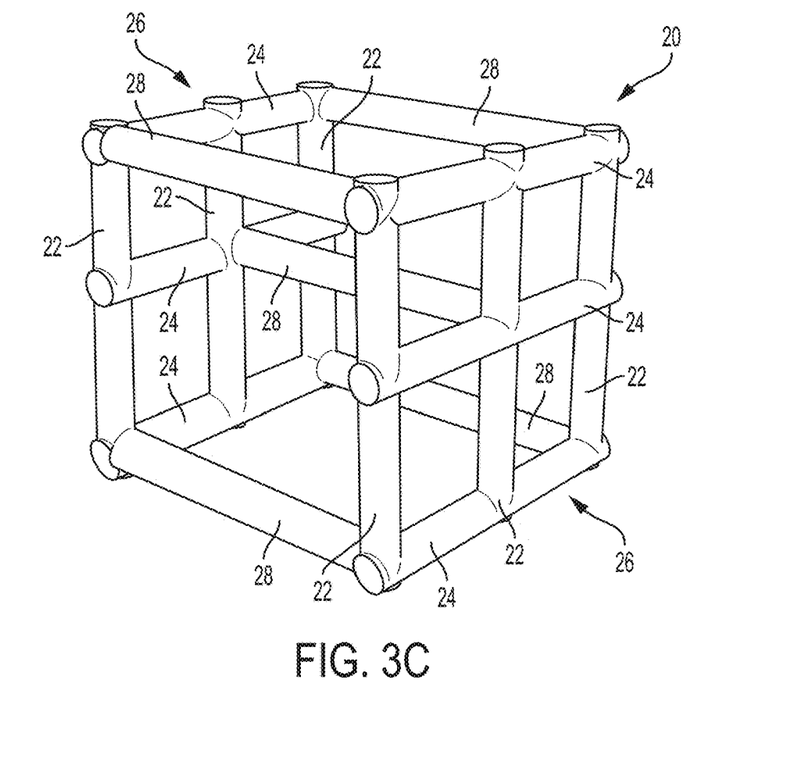

It will be recognized that FIG. 2 depicts an exemplary embodiment of a box or a cuboid skeleton which exemplarily constructs a rectangular scaffold and provides structural reinforcement in three dimensions of the scaffold. As depicted in FIGS. 3A-3C, the skeleton 20 may be constructed in a manner so as to provide structural support to the resulting scaffold in one or more dimensions. FIG. 3A exemplarily provides supports 22 aligned in a single direction. Alignment of the supports 22 in parallel within the scaffold generally provide mechanical support to the scaffold in a single direction, exemplarily in the dimension in which the supports 22 extend. While the supports 22 depicted in FIG. 3A are depicted as being vertical, it will be recognized that other orientations including extending in a depth or width dimension, or in another orientation thereto may fall within the scope of the present disclosure.

FIG. 3B depicts supports 22 which extend in a first direction and supports 24 which extend in a second direction. As exemplarily depicted in FIG. 3B, the first supports 22 intersect with at leas tone of the second supports 24 and the first support 22 are all parallel to one another while second supports 24 are parallel to each of the other second supports 24. While the embodiment of the skeleton 20 depicted in FIG. 3B depicts at least one first support 22 intersecting with at least one second support 24, it will recognized that not all of the first supports 22 and second supports 24 intersect one another, nor are they necessarily secured in a unitary structure. Therefore, as depicted in FIG. 3B, in exemplary embodiments of the skeleton 20, the skeleton 20 may include multiple support components, the support components each extending in a plane and/or dimension thus providing structural support to a resulting scaffold in two dimensions.

FIG. 3C depicts a still further exemplary embodiment of a skeleton 20, the skeleton 20 exemplarily providing structural support in three dimensions and exemplarily embodying a rectangular or cuboidal shape as exemplarily shown in the embodiment depicted in FIG. 2. In the skeleton depicted in FIG. 3C, the support component 26 are exemplarily connected by third supports 28 extending between the two support components. It will recognized that in other embodiments, for example, the skeleton 20 depicted in FIG. 2, that structural support in three dimensions may be provided by stacking layers of support extending in one or more directions to provide an extension of the skeleton 20 in a third dimension for structural support. While the exemplary embodiments depicted in FIGS. 3A-3C exemplarily depict generally rectangular skeletons 20, to produce generally rectangular scaffolds, it will be recognized that other shapes and/or configurations of skeletons and resulting scaffolds may be used within the scope of the present disclosure.

Figure 3D:
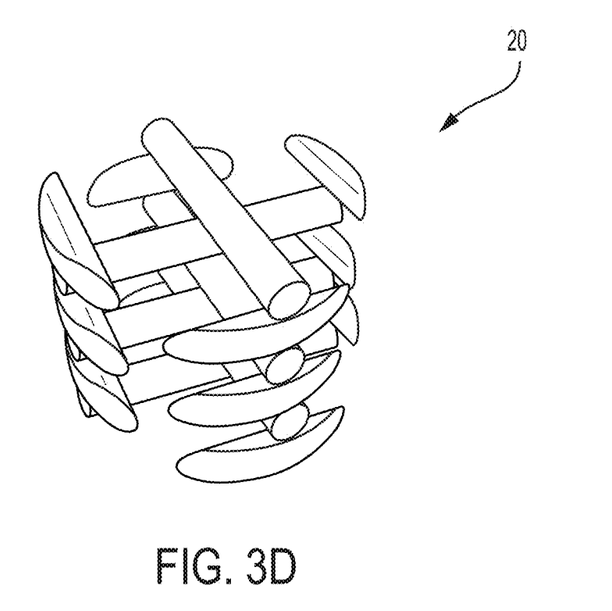
Figure 3E:
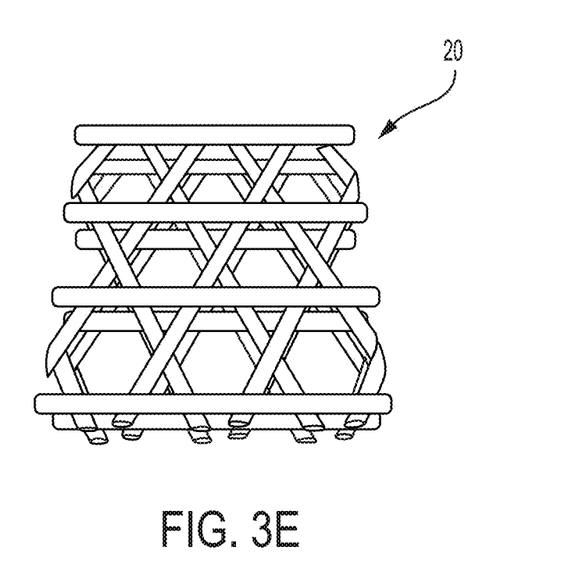
Figure 3F:
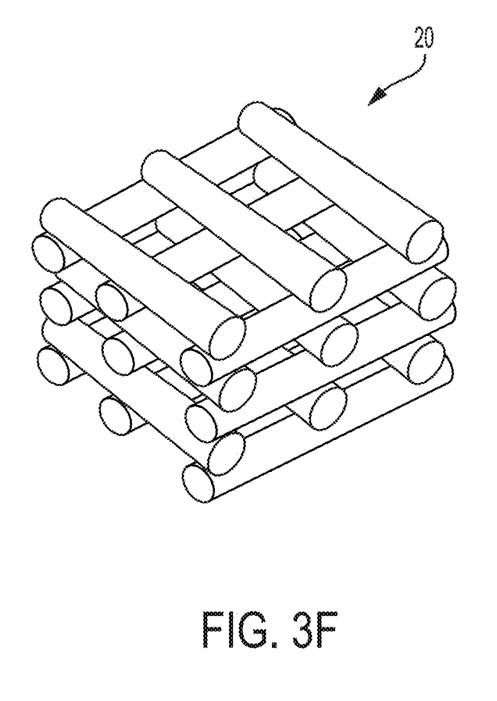

FIGS. 3D and 3E depict still further exemplary embodiments of arrangements for scaffolds 20. FIG. 3D depicts a scaffold that is cylindrical in shape in an exemplary embodiment, the skeleton 20 of the cylindrical scaffold can be constructed in a similar manner as the skeleton depicted in FIG. 2 although shaped in a cylindrical configuration, for example by truncating the skeleton about the corners. It will be recognized that in such an embodiment, that the skeleton is supported along the axis of the cylinder by sequential engagement of layers of orthogonally oriented supports.

FIG. 3E depicts a still further exemplary embodiment of a skeleton 20, for example arranged in a honey comb pattern by orienting multiple layers of supports. Each layer of supports being arranged in parallel to other supports in the layer, yet the supports in each layer being arranged at a different orientation than those supports in adjacent layers.

In the exemplary embodiment depicted in FIG. 3E, the layers may be exemplarily arranged at different non orthogonal angles to one another, for example 120 degrees relative to each of the adjacent layers as depicted in FIG. 3E. However, it will be recognized that other angles of orientations of the supports may be used in still further embodiments.

As exemplarily depicted with respect to FIGS. 2 and 3D, an arrangement of supports forming a skeleton may be modified to tailor the overall three dimensional shape of a resulting scaffold to the target or treatment area and to exemplarily align the supports of the skeleton with the predicted forces expected to be applied to the scaffold in vivo.

As depicted in FIG. 1, the host component 30 is exemplarily disposed within and around at least a portion of the skeleton 20 to full form the scaffold 10. In exemplary embodiments of the scaffold 10 disclosed in further detail herein, the host component 30 may be secured to the skeleton 20 in a variety of ways. Engagement between the host component 30 and the skeleton 20 helps to facilitate the transfer of force from the host component to the comparatively stronger and more resilient skeleton while further promoting the growth of bone tissue from and around the host component 30 about the supports of the skeleton 10 as the skeleton 10, particularly, as the skeleton 10 biodegrades over time.

As will be described in further detail herein, one or more securement methods may be used in embodiments of the disclosed scaffold to secure the host component 30 to the skeleton 20. In one exemplary embodiment, as described in further detail herein, when the scaffold is exemplarily constructed at an integrated body that includes both the skeleton and the host, the scaffold 10 may be a unitary structure. In an exemplary embodiment, the scaffold may be constructed using 3D printing and the skeleton and the host both constructed of the same material or of related materials of which the same material is the base component. In an exemplary embodiment, the combined skeleton and host component may be designed and constructed with varying levels of porosity, surface area, or density. This may be achieved by way of design, for example, by making the skeleton solidly out of material while the host component exhibits channeling, pores, or as a fibrous network that provides both the space for bone tissue growth, as well as faster biodegradation. It will be recognized that different properties in biodegradation and promotion of cell growth may further be achieved by 3D printing two or more materials that have the same base material as described herein, but with differing additive or secondary materials to impart different qualities between the skeleton and the host component. The commonality between the base material of both the skeleton and the host component facilitate bonding of the two structures with one another during 3D printing.

In embodiments of scaffolds as described herein, the host component may be molded into the skeleton, and the molded host component may physically interlock on a macroscale with macro interlock features which may be formed on the skeleton. Macro interlocking features may include pores that provide additional surface area for molded host component, or hooks, ridges, or other features of the skeleton to which the host component may physically interlock once molded. FIG. 3A exemplarily depicts various macro interlocking features, for example ridges 30, hooks 32, holes 34, or depressions 36. It will be recognized that while depicted in FIG. 3A, these macro interlock features may be exemplarily used on any of the embodiments as recognized by a person of ordinary skill in the art in view of the present disclosure.

Still other embodiments may be micro or nano physical interlocking. Micro and/or nano size interlocking features, for example pores, ridges, or other interlocking features on the surface of the skeleton may promote interlocking between the host component and the skeleton. In an exemplary and non-limiting embodiment, micro and nano scale physical interlocking may be used in an embodiment wherein the skeleton is ceramic and the host component is polymer and/or protein-based.

In additional exemplary embodiments, the skeleton and host component may intrinsically tend to for a physical bond. Surface modifications to one or both of the skeleton and/or host may further create or improve such disposition for physical bonding. In one exemplary embodiment, the skeleton is ceramic based and the host is polymer based, while in another embodiment, the skeleton is polymer based and the host component is ceramic based. In another exemplary embodiment, a polymer-based skeleton and a polymer-based host component may be also used in am embodiment to create physical bonds within the scaffold.

In another exemplary embodiment, chemical bonding integrates the skeleton and the host component. The skeleton and/or host component may include active functional groups that react with one another to form chemical bonds. In an exemplary embodiment, surface or bulk modification of one or more of the active functional groups of one or both of the skeleton and the host component may create or improve chemical reactions forming chemical bonding between the skeleton and the host component. In an exemplary embodiment, chemical bonding may occur when the skeleton is polymer based and the host component is polymer and/or protein-based.

TABLE 1

Mechanical properties of human bone tissue and different porous materials which may be employed for scaffold preparation.

| Scaffold components | | Mechanical properties | | |
|---|---|---|---|---|
| Polymer | Filler | Modulus (MPa) | Strength (MPa) | Porosity |
| PLLA | — | 2.2 | 1.8 | 87% |
| PLLA | Nano-HA | 14.9 | 8.7 | 85% |
| PLGA(50:50) | — | 8.33 | 1.2 | 92% |
| PLGA(50:50) | 40% CPC | — | 8.2 | — |
| PCL | — | — | 0.27 | — |
| PCL | HA | — | 0.57 | — |
| Chitosan | — | 4.5 | — | — |
| Chitosan | 2% Nano-HA | 8.6 | — | — |
| Gelatin | 50% BaG | 78 | 5.6 | 72% |
| Human cancelous bone | | 20-500 | 4-12 | 50-90% |
| Human cortical bone | | 3000-30000 | 130-180 | 5-10% |

The tradeoff between sufficient mechanical properties and porosity is one of the major challenges in designing tissue engineered constructs. For example, it has been observed in PLG scaffold that with increasing porosity from 80% to 92%, modulus dramatically decreases from 0.26 MPa to 0.0047 MPa (~50 times). Furthermore, in investigations, scaffolds are often tested mechanically in their dry state, thus the effect of aqueous medium of the body is neglected.

Many biocompatible and biodegradable polymers such as gelatin, collagen, or chitosan, which have been necessary in fabricating tissue scaffolds, considerably swell in aqueous mediums. In this case, modulus will be inversely related to water content. Swelling may cause remarkable decrease in modulus (~3 times) even in low water uptake (less than 5%). Scaffolds made from these polymers represent better mechanical properties (modulus in the range of 1-100 MPa) when tested in dry state, which does not mimic the environment of the human body. When the scaffolds fabricated from these materials are tested in swelled state, modulus can drop significantly (for example to less than 100 kPa).

With all of this being known, two or more different materials are selected to construct the scaffolds as disclosed herein. The following material may be used alone or in a composite to construct the skeleton and/or host component.

In embodiments, the skeleton and/or host component may be constructed at least partially of synthetic polymers including but not limited to: Poly($\alpha$-esters), for example, Polyglycolide, Polylactides, Poly(lactide-co-glycolide), Polydioxanone, Polycaprolactone, Poly(trimethylene carbonate), and Bacterial polyesters.

Aliphatic polyesters with reasonably short aliphatic chains between ester bonds can degrade over the time frame required for most of the biomedical applications. Poly($\alpha$-esters) comprise the earliest and most extensively investigated class of biodegradable polymers. They are attracting significant attention as biomaterials due to their good biocompatibility and controllable degradation profiles.

Due to the hydrogen bonding ability of the amide bonds and biodegradability imparted by the ester bonds, Poly(ester amine) co-polymers have good mechanical and thermal properties. The degradation of poly(ester amides) has been shown to take place by the hydrolytic cleavage of the ester bonds, leaving the amide segments more or less intact.

Poly(ortho esters) were developed by the ALZA corporation (Alzamers) as a hydrophobic, surface eroding polymer. Although the ortho ester linkages are hydrolytically labile, the polymer is hydrophobic enough such that its erosion in aqueous environments is very slow. The unique feature of poly(ortho esters) is that in addition to its surface erosion mechanism, the rate of degradation for these polymers, pH sensitivity, and glass transition Polyanhydrides can be considered as the most extensively investigated biodegradable surface eroding polymers. The hydrolytically labile backbone coupled with the hydrophobicity of the polymer precludes water penetration into the matrix allowing polyanhydrides to truly undergo surface erosion.

In still further exemplary embodiments of the skeleton and/or host component may be constructed in while or in part with: Polyurethanes, Poly(anhydride-co-imide), Cross-linked polyanhydrides, Poly(propylene fumarate), Pseudo poly(amino acid), Poly(alkyl cyanoacrylates), Polyphosphazenes, Polyphosphoest.

In other embodiments of the skeleton and/or host component, one or more natural polymers may exemplarily be used. Natural polymers may include proteins and poly (amino acids), for example: Collagen, Gelatin, Natural poly (amino acids), Synthetic poly(amino acids), Elastin, Elastin-like peptides, Albumin, or Fibrin. Natural polymers may further include polysaccharides, for example: Polysaccharides of human origin, or Polysaccharides of non-human origin.

In still further exemplary embodiment, other materials, including, but not limited to ceramics, metals, or hydrogels, which may be used purely or in the form of a composite may be used to construct either or both of the skeleton and host. Ceramics/Bioceramics/glasses for example may include, but are not limited to: Hydroxyapatite, Tricalcium phosphate, Calcium phosphate salts, and Bioactive glasses. Metals for example may include, but are not limited to: Magnesium or Iron. Hydrogels for example may include, but are not limited to gelatin, collagen, alginate, elastin, or hyaluronic acid.

It will be understood that the materials identified above will each have a natural rate of biodegradation as a property of the particular material. In addition, the degradability will further depend upon the physical construction of the skeleton and/or host component. The thickness of the skeleton and/or host component will lengthen a time to complete degradation. Increased porosity in the skeleton and/or host component will increase degradability of that structure. Therefore, by selection of material and physical construction of the skeleton and host components, the degradability of each component can be controlled and selected to match an estimated bone growth rate for the particular patient and physiological location within the patient.

The porosity and pore size of a scaffold and/or host material is dependent upon both the material (or materials) selected for the structure and preparation/manufacturing process used. By selection and control of the preparation/manufacturing process, the porosity and/or pore size, and therefore the resulting degradability of the skeleton and/or host component can be controlled.

As noted above, the addition of a skeleton with biocompatibility, high mechanical strength, and a comparatively slow biodegradability clearly increases the mechanical strength of the scaffold 10. New bone tissue growth is promoted by the host component 30 of the scaffold 10, the host component 30 having a structure and composition selected to promote bone growth at the treatment site.

Figure 4:
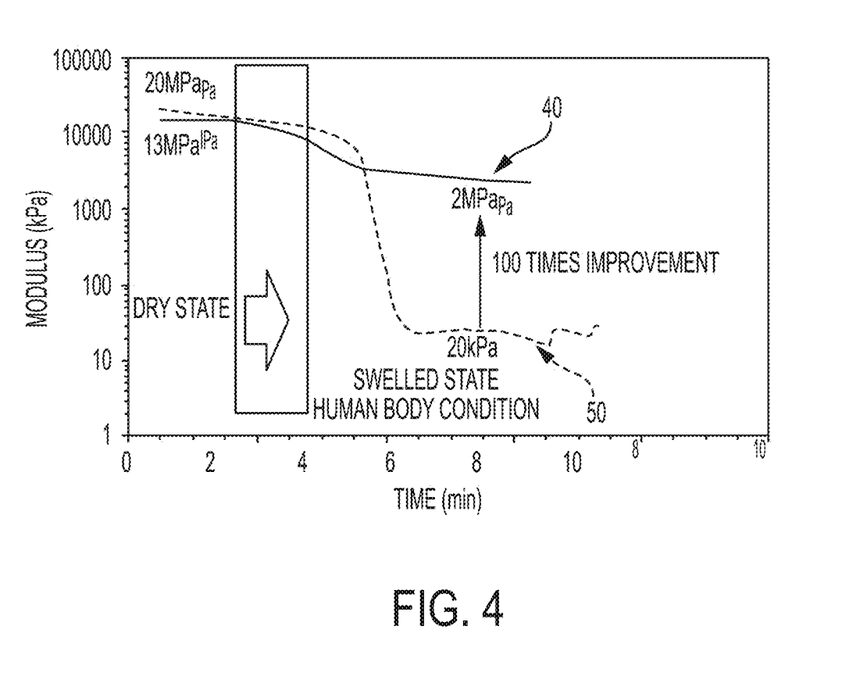
FIG. 4 is a graph depicting exemplary dynamic mechanical analysis test results of scaffolds.

FIG. 4 is a graph which depicts exemplary test results of a dynamic mechanical analysis comparing the modulus over time of an exemplary embodiment of the presently disclosed scaffold 40 as compared to the modulus overtime a scaffold of conventional construction 50. In this example, the embodiment of the new scaffold was constructed with a skeleton of Poly(L-lactide) polymer, CAS Registry number: 33135-50-1, which has an inherent viscosity of 0.9-1.2 dl/g in CHCl3 at 25° C. The host component is made of a composite of a matrix and a filler. The matrix is exemplarily Gelatin (CAS Registry number: 9000-70-8) from a porcine skin origin and a power form, Type A, and suitable for cell culture. The filler is exemplarily Hydroxyapatite (Calcium phosphate hydroxide, Durapatite, Hydroxylapatite), CAS Registry number: 1306-06-5. From FIG. 4, it can be observed that conventional scaffolds show a far greater decrease in modulus over time, in an aqueous environment, eventually resulting in an exemplary 100 fold decrease in the modulus compared to the presently disclosed embodiment upon reaching a steady state at approximately six minutes.

Figure 5:
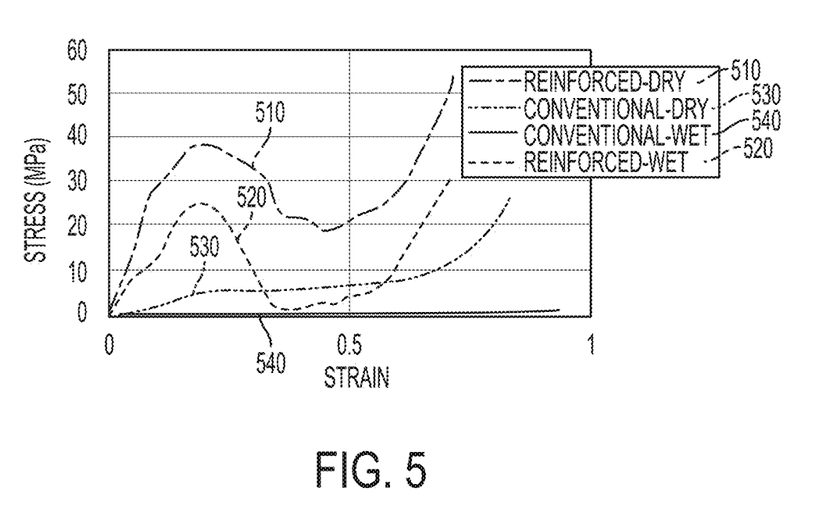
FIG. 5 is a graph depicting exemplary test results of stress versus strain measurements across various embodiments of scaffolds in dry and wet environments.

Similarly, FIGS. 4 and 5 are graphs that depict comparative exemplary test results of strength and stress measurements across various embodiments of scaffolds in different testing environments, namely dry and wet (aqueous) environments. The graph of FIG. 4 presents mechanical properties between conventional scaffolds in both wet and dry conditions and scaffolds of the present invention in both wet and dry conditions. In FIG. 5, the measured stress versus strain mechanical properties of the dry inventive scaffold 510 and the wet inventive scaffold 520 are compared. FIG. 5 shows significantly greater stress versus strain as compared to the measured mechanical properties of the dry conventional scaffold 530 and the wet conventional scaffold 540. Particularly with regard to comparison between the test results of the conventional scaffolds 540 and the test results of the inventive scaffolds 420 when both scaffolds were wet in an aqueous solution (the condition found within the human body) the stress versus strain property is approximately 375 times greater in the test results of the inventive scaffold 520 compared to the test results of the conventional scaffolds 540 tested.

In embodiments, the biodegradability of the skeleton of the scaffold provides for the structure and strength provided by the scaffold skeleton to be replaced over time with new bone tissue grown, providing the desired mechanical strength over a longer time period while also eliminating the need for additional surgery or recovery to replace non-biodegradable support. However, it will be recognized that different patients may experience different natural (or enhanced) rates of new bone tissue growth. Exemplarily patient's age, health, immune system, as well as the physiological location of the bone can effect the relative time required for complete new bone tissue growth. In embodiments, the material construction, and/or design of the skeleton can be modified or adjusted relative to an expected rate of new bone tissue growth. Additional drug or medical therapy treatments may increase a patient's natural rate of new bone tissue growth. In exemplary embodiments as disclosed herein, an expected rate of patient new bone tissue growth is determined and matched to an estimated rate of degradation of the scaffold skeleton. With the estimated rate of scaffold skeleton degradation matched to an estimated rate of new bone tissue growth, scaffold skeleton material is replaced with new bone tissue at approximately the same rate as the scaffold skeleton degrades, maintaining mechanical strength of the scaffold. As previously noted, the dimension (e.g. thickness), material, and porosity are characteristics of the scaffold skeleton that can be adjusted or selected for to achieve a desired rate of degradation.

Figure 6:
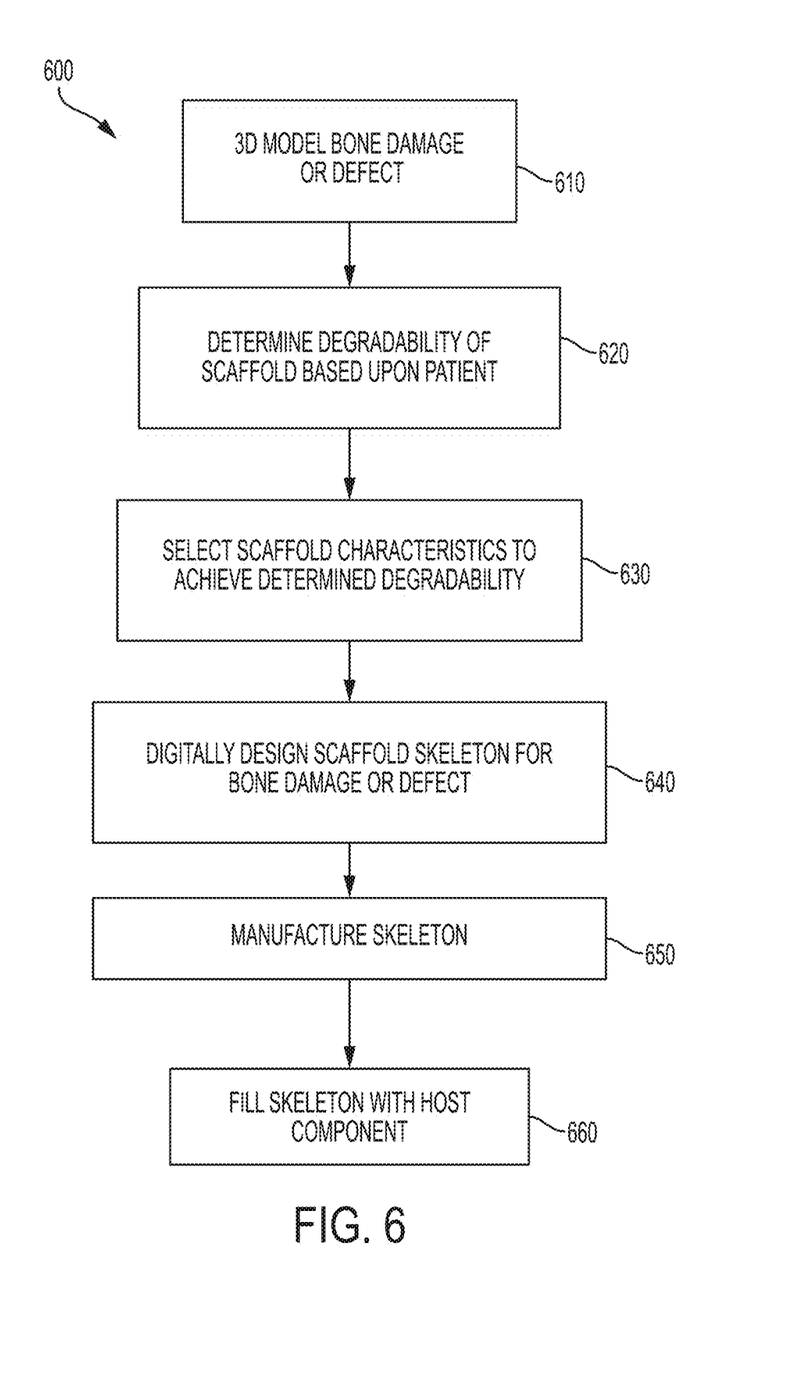
FIG. 6 is a flow chart depicting an exemplary embodiment of a method.

FIG. 6 is a flow chart that depicted an exemplary embodiment of a method 600 of manufacturing a scaffold for bone tissue growth. At 610 a 3D model of a bone damage or defect is created. In an exemplary embodiment, the size and shape of the bone damage or defect to be repaired with bone tissue engineering can significantly impact the scaffold needed. Particularly, the inventors have observed, that while bone damage or defects are often irregular in shape, those having a diameter, average diameter, or major axis of at least 1.5 cm or exemplarily between 1.5 cm-5 cm, or greater are in particular need of the improved mechanical strength provided by the embodiments of scaffolds as disclosed herein.

At 620 a degradability of the scaffold is determined based upon the patient to be treated. As noted above, patient age, health, immune response, as well as physiological location of the bone damage or defect can impact and expect a rate of new bone tissue growth and a degradability of the scaffold, and particularly the skeleton of the scaffold can be selected to correspond to the expected new bone tissue growth rate.

At 630 scaffold characteristics, and particularly scaffold skeleton characteristics, are selected to achieve the determined degradability. As noted above, the physical dimensions for example thickness or diameter of the supports of the skeleton may be adjusted to provide a scaffold with the determined degradability. The material or materials used to construct the skeleton and the porosity of the skeleton may be selected to achieve the determined degradability. For example, if a scaffold is desired to have a low degradability, meaning that it will take a long time to degrade, the thickness of the skeleton pieces can be increased, and a material with a slower biodegradability can be selected. On the other hand, if a scaffold is desired to degrade comparatively quickly, the thickness of the skeleton pieces may be reduced, porosity or other surface area may be added to the skeleton, or a material or materials with a faster biodegradability may be selected.

After the scaffold characteristics are selected, the scaffold skeleton is digitally designed specific to the bone damage of defect at 540. The shape and/or structure of the scaffold skeleton can be modified and matched to the shape, including the size of the patient bone damage or defect to be healed. In exemplary embodiments, any of, but not limited to, the skeleton designs described herein may exemplarily be used. In embodiments, the shape of the skeleton may be modified in those dimensions to provide a scaffold that fits the bone damage or defect. Also, depending upon the host component, the skeleton may be design with attached features, for example holes, ridges or hooks.

At 650 the digitally designed scaffold skeleton is manufactured. In exemplary embodiments, the scaffold skeleton may be manufactured with 3D printing, micro machining, injection molding, cast molding, or other known manufacturing techniques.

The following are examples of the preparation methods for the skeleton depending on the type of the material used: 3D printing, rapid prototyping, extrusion, molding, injection molding, and heating sintering.

After the scaffold skeleton is manufactured, then at 660 the skeleton is filled with the host component to complete the scaffold. As previously discussed, in one embodiments, the skeleton and the host component may be manufactured together simultaneously using 3D printing or other types of rapids prototyping. The host component is porous and constructed of a bioactive material which may, but not always include BMP. The host component promotes and facilitates a U-Bone tissue growth, particularly early in the new bone tissue growth process.

As discussed above, various techniques may be used in embodiments to connect or otherwise immobilize the host component relative to the skeleton. These techniques may include those discussed above. The techniques used to connect the host component to the skeleton, may further include, but are not limited to hydrolysis, aminolysis, plasma treatment, UV-induced copolymerization, ion-beam irradiation, ozone treatment, or surface-initiated atom transfer radial polymerization (ATRP). In still further exemplary embodiment, relative hydroxyl, carboxyl, a amine groups can be grafted onto the polymeric surfaces using γ-rsy irradiated, ozone, or photo-induced grafting to introduce hydrophilicity.

The following examples of the preparation method for the host component depending on the type of material used: freeze-drying, solvent casting/particulate leaching, gas foaming, porogen leaching, self-assembly, 3D printing, rapid prototyping, melt molding, fiber bonding, fiber mesh, membrane lamination, microsphere sintering, and replica template.

Figure 7:
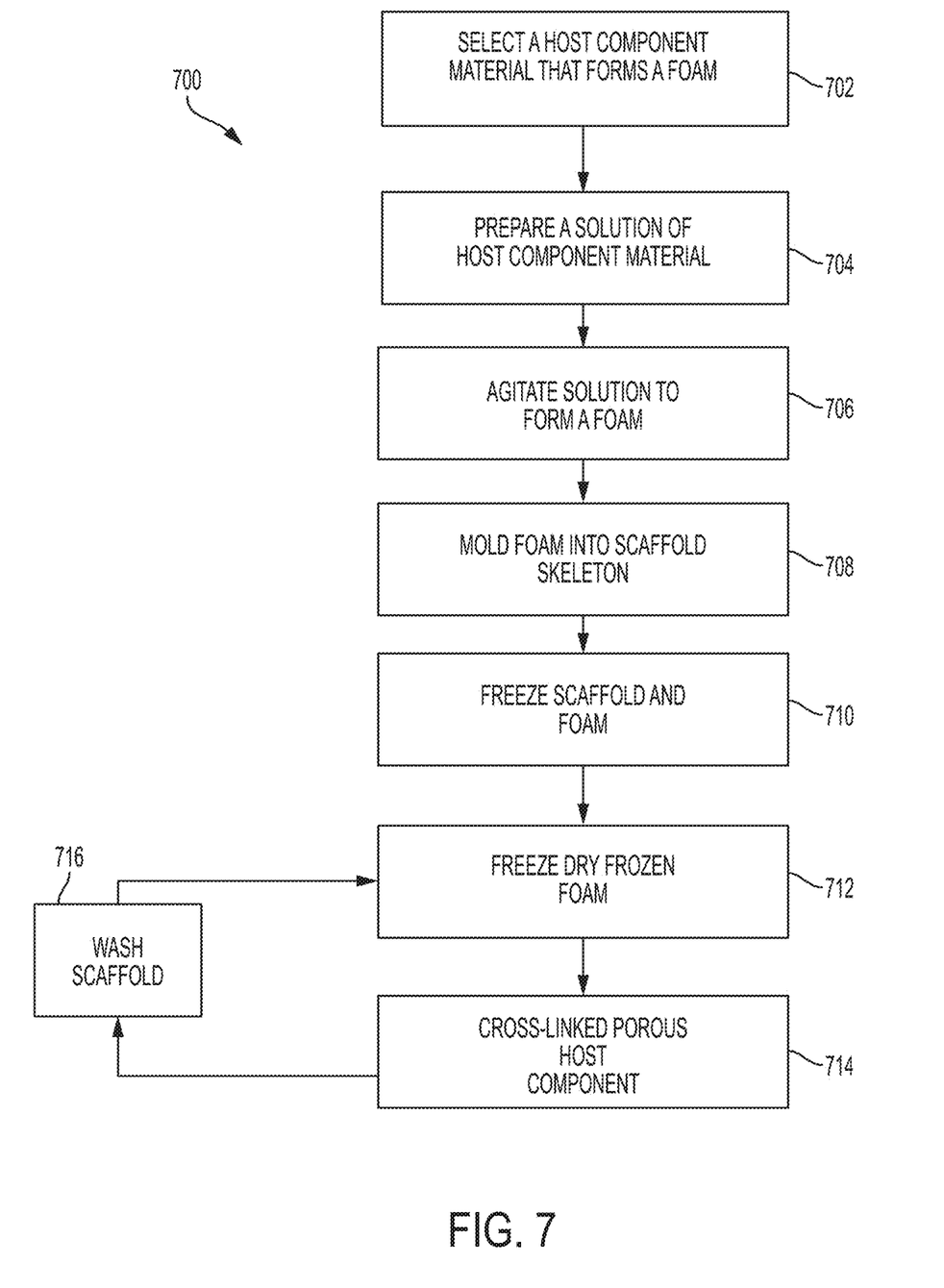
FIG. 7 is a flow chart depicting an exemplary embodiment of a method.

FIG. 7 is a flow chart that depicts an exemplary embodiment of a method 700 of constructing a scaffold in a manner that uses freeze-drying to produce porous structures for use as a host component. As previously noted, porosity is a desirable quality in a host component as the porosity both facilitates bone tissue growth by providing space within which bone cells can grow and spread while the porosity also increases a degradation rate of the host component providing additional space within which the new bone tissue can replace the volume previously held by the host component. With exemplary embodiments of the scaffold relying more on the skeleton of the scaffold for the mechanical strength of the scaffold, a more porous host component can be used.

In the exemplary embodiment of the method 700, at 702 a host component material is selected. The selected host component material is a material that is capable of forming a foam through agitation as described in further detail herein. In exemplary embodiments, this may include a polymer, a protein, or a composite material comprising one or both of these materials. In still further exemplary embodiments a material that does not have a foaming capability may be combined with a selected host component material that forms a foam, such that a combination of material has a foaming capability. In one exemplary embodiment, a ceramic may be added to a material that foams such that the host component has ceramic qualities while still being able to form a foam under agitation. In still further examples of materials that are capable of forming foams including gelatin, collagen, albumin, and others as may be recognized by a person of ordinary skill in the art in view of the present disclosure. It will be recognized that other materials which are not capable of forming a foam may be used for the host component, although one of the other preparation methods as noted above may be used. The method 700 as described herein is exemplarily one method of preparing a scaffold, and it will be recognized that other procedures may fall within the scope of the present disclosure.

At 704, a solution is prepared of the host component material or combination of materials. In an exemplary embodiment, any solvent that can be removed through sublimation may be used to prepare the solution at 704. In an exemplary and non-limiting embodiment, the solvent is water. In preparing the solution at 704, the concentration of the solution may exemplarily by between 1-50% weight/volume. In a further exemplary embodiment, the concentration of the solution is between 2-20% weight/volume. In a still further exemplary embodiment, the concentration of the solution is between 5-15% weight/volume.

Next, at 706 the solution is agitated to form a foam. In exemplary embodiments, the solution is agitated at a predetermined speed for a predetermined time using for example a mechanical stirrer, homogenizer, or sonicator until a foam-like fluid is obtained. The particular agitator, agitation speed, and agitation time may exemplarily depend on the specific host component material or materials being agitated or, for example, laboratory environmental conditions. In am exemplary embodiment, the agitation speed using mechanical stirrer may exemplarily be between 100-40,000 RPM. In a further exemplary embodiment, the agitation speed using a mechanical stirrer is between 300-20,000 RPM. In a still further exemplary embodiment, the agitation speed using a mechanical stirrer may be between 500-5,000 RPM. The time of the agitation may exemplarily depend, at least in part, upon the agitation speed and may exemplarily be between 1-60 minutes. In a further exemplary embodiment, the time of agitation may exemplarily be between 5-45 minutes. In a still further exemplary embodiment, the agitation time may be between 10-30 minutes.

After the solution of host component material has been agitated into a foam, the foam is molded into the scaffold skeleton at 708. The scaffold skeleton may be any of those as previously described herein. With the foam molded into the scaffold skeleton, the scaffold is created. The scaffold including the skeleton and the now molded foam is transferred into a freezer to freeze the scaffold and foam at 710. In an exemplary embodiment, the temperature of the freezer may be between 0--200° C. In an exemplary embodiment, the freezer temperature may be −80° C.

Once the foam is frozen within the skeleton of the scaffold, the scaffold is freeze-dried at 712. The freeze-drying process of the frozen foam produces a porous host component that may be exemplarily cross-linked. If it is required, the host component may contain different cross-linkers which may include, but are not limited to glutaldehyde, EDC/NHS, paraformaldehyde, and others as would recognized by a person of ordinary skill in the art.

This process produces a cross-linked porous host component at 714 that is held within the scaffold skeleton to produce a scaffold as described above.

It will be recognized that in some embodiments, in order to promote cross-linking, optional steps of washing the scaffold at 716 followed by freeze-drying the washed scaffold may be performed to produce the final cross-linked porous host component of the scaffold.

In exemplary embodiments, the skeleton and host component are chemically bound to form the scaffold. In the exemplary embodiments, a polymer such as PCL, PLA, or PLGA is used for skeleton and gelatin is used as the host.

A first exemplary embodiment uses Aminolysis and gelatin immobilization. The skeleton (e.g. PCL) is immersed in isopropanol solution of 1,6-hexanediamine at 40° C. After aminolysis treatment, the skeleton is rinsed with deionized water to remove free 1,6-hexanediamine, and dried in a vacuum oven. The aminolyzed skeleton is immersed in cross-linker, for example, glutaraldehyde or EDC/NHS. Gelatin foam prepared by agitation is added to the construct. The whole construct is transferred to −80° C., and then freeze-dried. The whole construct will be cross-linked using EDC/NHS or glutaraldehyde, washed with water and freeze-dried again to obtain the bonded scaffold.

A second exemplary embodiment uses surface-initiated ATRP or GMA and conjuration of gelatin. In this example, after aminolysis treatment, alkyl halide STRP initiator is introduced in the PCL-$NH_2$ surface through the reaction of the amine groups with 2-bromoisobutyrate bromine (BIBB). After washing and drying, surface-initiated ATRP of GMA is carried out to generate the PCL-g-P (GMA). Gelatin form is then incubated with the treated PCL to couple it onto pendant epoxide groups. The result is freeze-dried and then cross-linked, for example using EDC-NHS or glutaraldehyde. The result is washed with water and freeze-dried again to obtain the bonded scaffold.

After the scaffold, including the skeleton and host component is constructed, the entire scaffold may be inserted into the bone damage or defect. Surrounding area between the scaffold and the existing bone in the patient may further be filled if host component which may be the same material and/or materials as the host component of the scaffold, or another material or materials.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A scaffold for use in bone tissue engineering, the scaffold comprising:
   a skeleton constructed to form a three-dimensional shape defining a space, the skeleton constructed of a first material and having a first rate of biodegradation; and
   a host component filling the space defined by the three-dimensional shape formed by the skeleton, the host component constructed of a second material and having a second rate of biodegradation, wherein the first rate of biodegradation is slower than the second rate of biodegradation;
   wherein the skeleton and the host component form a unitary structure constructed throughout as an integrated body.

2. The scaffold of claim 1, wherein the skeleton is a solid construction consisting of the first material and the host component consists of the second material which is porous.

3. The scaffold of claim 1, wherein the host component further comprises bone morphogenetic proteins.

4. The scaffold of claim 1, wherein the second material is a foam.

5. The scaffold of claim 1, wherein the host component is a scaffold host component, and wherein further host material surrounds the skeleton, wherein the further host material is the second material or a third material.

6. The scaffold of claim 1, wherein a first dimensional plane through the scaffold comprises both a first portion of the skeleton and a first portion of the host component, and wherein the first dimensional plane is oriented in a direction of the expected forces to be applied to the first portion of the skeleton in vivo.

7. The scaffold of claim 1, wherein a first dimensional plane through the scaffold comprises both a first portion of the skeleton and a first portion of the host component and a second dimensional plane, orthogonal to the first dimensional plane, comprises both a second portion of the skeleton and a second portion of the host component.

8. The scaffold of claim 7, wherein the skeleton comprises:
   a plurality of first supports, each of the first supports aligned in parallel to the other first supports; and
   a plurality of second supports, each of the second supports aligned in parallel to the other second supports and oriented at an angle different from an angle of the first supports.

9. The scaffold of claim 8, wherein the skeleton further comprises a plurality of third supports, each of the third supports aligned in parallel to the other third supports and oriented at an angle different from the angle of the first supports and the angle of the second supports.

10. The scaffold of claim 1, wherein the host component is molded into the space defined by the three-dimensional shape formed by the skeleton, and forms the unitary structure by macroscale, microscale, or nanoscale physical interlocking between the host component and the skeleton.

11. The scaffold of claim 1, wherein the skeleton further comprises:
   a chemical surface treatment to promote bonding between the host component and the skeleton;
   wherein the chemical surface treatment is selected from hydrolysis, aminolysis, plasma treatment, ozone treatment, or surface-initiated atom transfer radial polymerization (ATRP).

* * * * *